United States Patent
Mahr et al.

(10) Patent No.: US 7,319,119 B2
(45) Date of Patent: Jan. 15, 2008

(54) OIL-IN-WATER EMULSIONS OF AMINOSILOXANES

(75) Inventors: Günter Mahr, Burghausen (DE); Franz X. Wimmer, Burghausen (DE); Willibald Burger, Burghausen (DE); Ludwig Esterbauer, Ampfing (DE)

(73) Assignee: Wacker Chemie AG, Munich (DE)

( * ) Notice: Subject to any disclaimer, the term of this patent is extended or adjusted under 35 U.S.C. 154(b) by 233 days.

(21) Appl. No.: 11/007,555

(22) Filed: Dec. 8, 2004

(65) Prior Publication Data

US 2006/0041026 A1    Feb. 23, 2006

(30) Foreign Application Priority Data

Aug. 19, 2004  (DE)  ............... 10 2004 040 266

(51) Int. Cl.
*C08L 83/08* (2006.01)
(52) U.S. Cl. .................... 524/588; 516/55
(58) Field of Classification Search ............ None
See application file for complete search history.

(56) References Cited

U.S. PATENT DOCUMENTS

| 4,757,106 A | 7/1988 | Mayer et al. |
| 5,336,715 A | 8/1994 | Sejpka et al. |
| 6,294,608 B1 | 9/2001 | Hager et al. |
| 6,596,060 B1 | 7/2003 | Michaud |
| 6,921,788 B1 * | 7/2005 | Izawa et al. ............ 524/430 |
| 2004/0029981 A1 | 2/2004 | Herzig et al. |

FOREIGN PATENT DOCUMENTS

| DE | 4 328917 | 3/1995 |
| EP | 0 068 671 | 1/1983 |
| EP | 0 186 265 | 7/1986 |
| EP | 0 242 798 | 10/1987 |
| EP | 0 556 740 A1 | 8/1993 |
| EP | 1 008 616 A2 | 6/2000 |
| EP | 1 031 593 | 8/2000 |
| GB | 1199501 | 7/1970 |
| WO | 01/32792 * | 5/2001 |

OTHER PUBLICATIONS

Derwent Abstract corresponding to de 4 328 917 [an 1995-099369].
Derwent Abstract corresponding to EP 1 008 616 [AN 2000-432896].
Derwent Abstract corresponding to EP 1 031 593 [AN 2000-573635].
Derwent Abstract corresponding to EP 0 242 798 [AN 1987-300490].
Derwent Abstract corresponding to EP 0 556 740 [AN 1993-265473].

* cited by examiner

Primary Examiner—Kuo-Liang Peng
(74) Attorney, Agent, or Firm—Brooks Kushman P.C.

(57) ABSTRACT

Oil-in-water emulsions which contain
(i) 100 parts by weight of a polydimethylsiloxane (P) having aminoalkyl groups and having an amine number of at least 0.1 meq/g of polydimethylsiloxane (P), composed of units of the general formula I $$R^1_a R^2_b SiO_{(4-a-b/2)}, \qquad (I)$$

in which $R^2$ are aminoalkyl radials of the formula II $$-R^3-NR^4R^5,, \qquad (II)$$

(ii) protonating agent,
(iii) water and
(iv) not more than 5 parts by weight of emulsifier, are stable and provide for improved water repellency of porous and nonporous, absorptive and non-absorptive substrates treated therewith.

12 Claims, No Drawings

OIL-IN-WATER EMULSIONS OF AMINOSILOXANES

BACKGROUND OF THE INVENTION

1. Field of the Invention

The invention relates to oil-in-water emulsions of polydimethylsiloxanes having aminoalkyl groups and the use thereof.

2. Background Art

Solvent-based compositions based on amino-functional polydimethylsiloxanes which are used, for example, as water-repellant care compositions are known. U.S. Pat. No. 6,596,060, Atofina, P. Michaud, describes a water-repellant composition which comprises an organopolysiloxane having at least one aminated group and 85-99% by weight of isopropanol. Solvent-based compositions based on (amino-functional) organopolysiloxanes are generally distinguished by a very good water-repellant effect on a very wide range of substrates but are no longer contemporary both in terms of increased environmental awareness with respect to volatile organic compounds (VOCs) and also from the point of view of health. Aqueous compositions will in general therefore increasingly replace solvent-based systems in the future.

Aqueous compositions which contain amino-functional organopolysiloxanes are known. Such compositions are used, for example, for the water-repellant treatment of natural and/or synthetic textile fibers, for the water-repellant treatment of building materials, as a component of polish compositions and as a component of cosmetic formulations. Conventional aqueous compositions which contain amino-functional organopolysiloxanes are known to a person skilled in the art in the form of oil-in-water or water-in-oil emulsions. These emulsions may be present in the form of macroemulsions or microemulsion, and are stabilized, as a rule, by conventional nonionic, anionic, cationic, or amphoteric emulsifiers or by silicone/polyether copolymer emulsifiers.

DE 4328917, Wacker-Chemie GmbH, M. Geck, describes a process for the preparation of microemulsions based on amino-functional organopolysiloxanes, in which organopolysiloxane, conventional emulsifier, water, optionally a cosurfactant and optionally an acid, are combined in any desired sequence and mixed. However, the presence of nonionic, anionic, cationic or amphoteric emulsifiers in these aqueous compositions which contain amino-functional organopolysiloxanes has a considerable, sometimes even drastic, effect on the water-repellant properties of such emulsions in the application.

Aqueous compositions which contain amino-functional organopolysiloxanes and which dispense with the use of the abovementioned conventional emulsifiers are also known. GB 1199501 describes water repellants, in particular for glass surfaces, which contain isopropanol, water and a reaction product of a hydroxyl-terminated, basic nitrogen-containing organopolysiloxane with organic or inorganic acids. However, the aqueous dilutions of these water repellants do not have sufficient stability of the active substance.

EP 1008616 A describes w/o emulsions which contain amino-functional organopolysiloxanes. Such emulsions have the disadvantage that they have a predetermined composition and cannot be diluted with water.

EP 1031593 A describes a composition which consists of a mixture of water-soluble, amino-functional silicon compounds substantially free of alkoxy groups, water, optionally alcohol and optionally acid. The water-repellant effect of the composition is greatly limited by the use of water-soluble (partial) condensates of water-soluble aminosilanes.

EP 186265 A and EP 68671 A describe compositions which contain (1) a mixture of a salt (A) of an organopolysiloxane having at least one amino group and at least one reactive group —OX, in which X is a hydrogen atom, alkyl radical or alkoxyalkyl radical, with (B), an organosilicon compound soluble in (2) and having at least two reactive groups —OX, and (2) a water-soluble solvent. The aqueous dilutions of these compositions do not have sufficient stability of the active substance.

EP 242798 A describes aqueous emulsions which contain, as emulsifiers, the salt of a water-soluble organic or inorganic acid and polysiloxane which, in addition to other siloxane units, contains siloxane units which have monovalent, SiC-bonded radicals comprising basic nitrogen in amounts of at least 0.5 percent by weight of basic nitrogen, based on the weight of the polysiloxane. As is known, such emulsions are not stable to dilution over a relatively long period.

EP 556740 A describes organopolysiloxane compositions which contain a salt of a water-soluble organic or inorganic acid and an organopolysiloxane which has at least one SiC-bonded organic radical comprising basic nitrogen. Such compositions have an active substance which is stable on dilution but are not adequate in their water-repellant effect.

U.S. 2004/0029981 A describes the treatment of fibers with emulsifier-free emulsions of amino-functional silicone oils.

SUMMARY OF THE INVENTION

It is an object of the invention to provide aqueous compositions which do not have the above-mentioned disadvantages. This and other objects are achieved by oil in water emulsions of at least one polydimethylsiloxane (P) having aminoalkyl groups and having an amine number of at least 0.1 meq/g of polydimethylsiloxane (P), composed of units of the general formula I $$R^1_a R^2_b SiO_{(4-a-b/2)} \quad (I),$$

in which $R^2$ are aminoalkyl radicals.

DETAILED DESCRIPTION OF THE PREFERRED EMBODIMENT(S)

The invention thus relates to oil-in-water emulsions which contain (i) 100 parts by weight of at least one polydimethylsiloxane (P) having aminoalkyl groups and having an amine number of at least 0.1 meq/g of polydimethylsiloxane (P), comprising units of the general formula I $$R^1_a R^2_b SiO_{(4-a-/2)} \quad (I)$$

in which $R^1$ are independently optionally halogen-substituted alkyl radicals having 1-40 carbon atoms, or —OR or —OH radicals, R are independently optionally halogen-substituted alkyl radicals having 1-40 carbon atoms, $R^2$ are independently aminoalkyl radicals of the general formula II $$-R^3-NR^4R^5 \quad (II)$$

$R^3$ are independently divalent hydrocarbon radicals having 1-40 carbon atoms, $R^4$ are independently monovalent hydrocarbon radicals having 1-40 carbon atoms or H, $R^5$ independently are radicals of the general formula III $$—(R^6—NR^4)_xR^4 \quad (III)$$

$R^6$ independently are divalent radicals of the general formula IV $$—(CR^4R^4—)_y \quad (IV)$$

x is 0 or a value from 1 to 40,
y is value 1 or 2,
a is 0, 1, 2 or 3,
b is 0, 1, 2 or 3,
a+b on average is from 1 to 2.5, and
not more than 9 mol % of the radicals $R^1$ being OH or OR,
(ii) protonating agents,
(iii) water, and
(iv) not more than 5 parts by weight of emulsifier.

The emulsions are homogeneous, stable and stable to dilution without further addition of other stabilizing ingredients, such as emulsifiers or silicone/polyether copolymers. They preferably contain not more than 3, more preferably not more than 1, and in particular not more than 0.1, parts by weight of emulsifier. The compositions are preferably emulsifier-free.

The alkyl radicals $R^1$ and R may be linear, cyclic, branched, saturated or unsaturated. The alkyl radicals $R^1$ and R preferably have 1-18 carbon atoms, in particular 1-6 carbon atoms, and the methyl radical or ethyl radical is particularly preferred. Preferred halogen substituents are fluorine and chlorine. Particularly preferred radicals $R^1$ are the methyl radical, methoxy radical, ethoxy radical or —OH.

The divalent hydrocarbon radicals $R^3$ may be halogen-substituted, linear, cyclic, branched, aromatic, saturated or unsaturated. The radicals $R^3$ preferably have 1 to 6 carbon atoms, and alkylene radicals are particularly preferred, in particular propylene. Preferred halogen substituents are fluorine and chlorine.

The monovalent hydrocarbon radicals $R^4$ may be halogen-substituted, linear, cyclic, branched, aromatic, saturated or unsaturated. The radicals $R^4$ preferably have 1 to 6 carbon atoms, and alkyl radicals are particularly preferred. Preferred halogen substituents are fluorine and chlorine. Particularly preferred substituents $R^4$ are methyl, ethyl, cyclohexyl and H.

In the polydimethylsiloxanes, b preferably has the value 0 or 1, and a+b preferably has an average value of from 1.9 to 2.2.

In the polydimethylsiloxanes, x is preferably 0 or a value from 1 to 18, most preferably from 1 to 6.

Particularly preferred radicals $R^2$ are —$CH_2N(R^4)_2$, —$(CH_2)_3N(R^4)_2$, —, and $(CH_2)_3N(R^4)(CH_2)_2N(R^4)_2$.

The polydimethylsiloxane (P) is composed of at least 3, in particular at least 10, units of the general formula I.

The ratio of a to b is chosen so that the polydimethylsiloxane (P) has an amine number of at least 0.1 meq/g of polydimethylsiloxane (P), preferably at least 0.6 meq/g of polydimethylsiloxane (P). The amine number of the polydimethylsiloxane (P) is preferably not more than 7 meq/g of polydimethylsiloxane (P). The viscosity of the polydimethylsiloxane (P) is preferably from 1 to 100,000 mPa·s, in particular from 10 to 10,000 mPa·s, at 25° C.

The emulsions preferably contain auxiliaries which are selected from mono- or polyalcohols and ethers thereof, which have a boiling point or boiling range of not more than 260° C. at 0.10 MPa.

The protonating agent is preferably a monoprotic or polyprotic, water-soluble or water-insoluble, organic or inorganic acid, most preferably formic acid, acetic acid, sulfuric acid, hydrochloric acid or citric acid. The protonating agent is preferably added in an amount of from 0.05 to 2 mol of acidic proton per mole of basic nitrogen atom of the radicals $R^2$.

The water is demineralized or non-demineralized water, preferably demineralized water.

In a preferred embodiment, the emulsions contain MQ silicone resin. The MQ silicone resin preferably contains at least 80 mol %, preferably at least 95 mol %, of units of the general formulae V and VI $$R^7_3SiO_{1/2} \quad (V),$$

$$SiO_{4/2} \quad (VI),$$

in which
$R^7$ are optionally halogen-substituted hydrocarbon radicals having 1-40 carbon atoms or H, —OR or —OH radicals, and the ratio of the units of the general formulae V and VI is from 0.5 to 2.0, preferably from 0.5 to 1.5, and not more than 3% by weight, preferably not more than 2.5% by weight, of the radicals $R^7$ are —OR and —OH.

The remaining units of the MQ silicone resin are preferably units of the general formulae VII and VIII $$R^7_2SiO_{2/2} \quad (VII),$$

$$R^7SiO_{3/2} \quad (VIII).$$

The monovalent hydrocarbon radicals $R^7$ may be halogen-substituted, linear, cyclic, branched, aromatic, saturated or unsaturated. The radicals $R^7$ preferably have 1 to 6 carbon atoms, and alkyl radicals and phenyl radicals are particularly preferred. Further halogen substituents are fluorine and chlorine. Particularly preferred substituents $R^7$ are methyl, ethyl, phenyl and H.

The emulsions preferably contain from 1 to 200 parts by weight, particularly preferably from 5 to 100 parts by weight, of MQ silicone resin.

The emulsions can be easily prepared by combining and mixing the individual components in any desired sequence.

The invention furthermore relates to the use of the emulsions for the treatment, and preferably for the water-repellant treatment, of porous or nonporous, absorptive or non-absorptive substrates, preferably of celluloses, paper, natural and/or synthetic textile fibers, mineral building materials, stone, tiles, marble, metals, painted metals, glass, ceramics, glass ceramic, plastics, coated plastics, wood, laminate, cork, rubber, imitation leather and leather. The uses of the emulsions for the sizing of paper and coating of gypsum plasterboard and as care compositions are particularly preferred.

All above symbols of the above formulae and in the claims have their meanings in each case independently of one another. In all formulae, the silicon atom is tetravalent.

In the following examples, all stated amounts and percentages are based on weight, all pressures are 0.10 MPa (abs.) and all temperatures are 20° C., in each case unless stated otherwise.

EXAMPLES

Part A
1. In order to demonstrate the advantage of the emulsions according to the invention, they were tested in comparison with aqueous, emulsifier-containing compositions and a solvent-based composition, based in each case on the same active substance, with respect to their water-repellant effect.

For porous substrates, the impregnating effect was tested on wood (beech and spruce) and untreated leather.

For nonporous substrates, the water repellency on automotive finish was tested by means of the contact angle.

The amino-functional organopolysiloxane having the functional groups —$(CH_2)_3NH(CH_2)_2NH_2$ and used in the test examples has a viscosity of about 1000 mm²/s at 20° C. and an amine number of 0.6 meq/g of organopolysiloxane. This organopolysiloxane is referred to below simply as "amine oil."

Preparation of Various Compositions:

Aqueous Composition A According to the Invention:

17 g of the amine oil are added to 6 g of water, 6 g of ethylene glycol monobutyl ether and 0.16 g of acetic acid at room temperature while stirring, and a further 70.84 g of water are then stirred in. A milky opaque emulsion is obtained. For the application test, the emulsion is diluted to an active substance content of 5% with demineralized water.

COMPARATIVE EXAMPLE 1

Aqueous, Emulsifier-Containing Composition B 17 g of the amine oil are added to 6 g of water, 6 g of emulsifier (fatty alcohol ethoxylate having about 6 EO) and 0.16 g of acetic acid at room temperature while stirring, and a further 70.84 g of water are then stirred in. A milky opaque emulsion is obtained. For the application test, the emulsion is diluted to an active substance content of 5% with demineralized water.

COMPARATIVE EXAMPLE 2

Benzinic Composition C 5 g of amine oil are dissolved in 95 g of benzine 100/140 at room temperature while stirring. A clear solution is obtained.

Aqueous Composition A1 According to the Invention:

17 g of a mixture of 13.6 g of amine oil and 3.4 g of MQ silicone resin are added to 7 g of water, 7 g of ethylene glycol monobutyl ether and 0.13 g of acetic acid at room temperature while stirring, and a further 68.87 g of water are then stirred in. A milky opaque emulsion is obtained. For the application test, the emulsion is diluted to an active substance content of 5% with demineralized water.

COMPARATIVE EXAMPLE 3

Aqueous, Emulsifier-Containing Composition B1

17 g of a mixture of 13.6 g of amine oil and 3.4 g of MQ silicone resin are added to 7 g of water, 7 g of emulsifier (fatty alcohol ethoxylate having about 5 EO) and 0.13 g of acetic acid at room temperature while stirring, and a further 68.87 g of water are then stirred in. A milky opaque emulsion is obtained. For the application test, the emulsion is diluted to an active substance content of 5% with demineralized water.

1.1. Testing on Porous Surfaces 1.1.1. Use on Wood (Beech, Spruce)

Wood cubes having an edge length of 30 mm are used for testing. These are immersed with a face 5 mm deep in the corresponding formulation for 1 nin. After a drying time of 14 days at room temperature (22° C.), the tests are carried out. The water-repellant effect is determined by two different methods: Firstly by measuring the contact angle of a water drop on the treated surfaces (beech and spruce) and secondly by determining the weight increase (beech) on immersion in water by weighing.

1.1.1.1. Determination of the Contact Angle of a Water Drop

A 0.04 ml water drop is placed on the end faces of the treated wood cubes and the contact angle [°] of the water drop is determined. In each case the mean value of three measurements is determined. The results are shown in Table 1:

TABLE 1

|  | Untreated | Formulation A | Formulation B Comparative Example 1 | Formulation C Comparative Example 2 |
|---|---|---|---|---|
|  | Contact angle [°] | | | |
| Beech: | | | | |
| immediately | not measurable, immediately absorbed | 150 | 140 | 130 |
| after 1 min. | — | 149 | 100 | 125 |
| after 2 min. | — | 148 | 85 | 120 |
| after 3 min. | — | 148 | 75 | 118 |
| Spruce: | | | | |
| immediately | not measurable, immediately absorbed | 125 | 125 | 105 |
| after 1 min. | — | 125 | 55 | 104 |
| after 2 min. | — | 125 | 20 | 103 |
| after 3 min. | — | 125 | — | 103 |

1.1.1.2. Determination of the Weight Increase

After a drying time of 14 days at room temperature (22° C.), the beech cubes are weighed (g1) and then immersed with the treated side 3 mm deep in water for 30 min and the weight (g2) is determined again. The smaller the resulting weight increase the better impregnated is the wood. Results are shown in tables 2 and 3.

Calculation of the Weight Increase in [%]:

$$\Delta g = (g2-g1)/g2 \times 100$$

TABLE 2

|  |  | g1 [g] | g2 [g] | Δ g [g] | Δ g [%] |
|---|---|---|---|---|---|
| Untreated beech |  | 19.7997 | 27.6791 | 7.8794 | 28.5 |
| Composition A: | aqueous | 19.7511 | 20.0344 | 0.2833 | 1.4 |
| Composition B: (Comparative Example 1) | aqueous | 19.6554 | 27.4516 | 7.7962 | 28.4 |
| Composition C: (Comparative Example 2) | benzinic | 19.9725 | 20.1202 | 0.1477 | 0.7 |

Surprisingly, both test methods show that the composition A according to the invention is substantially superior to the conventional composition B, and the benzinic composition C is substantially equivalent with respect to the impregnation effect.

TABLE 3

|  |  | g1 [g] | g2 [g] | Δ g [g] | Δ g [%] |
|---|---|---|---|---|---|
| Untreated beech |  | 18.6501 | 28.6954 | 10.0453 | 35.0 |
| Composition A1: | aqueous | 18.3933 | 18.8922 | 0.4989 | 2.6 |
| Composition B1: (Comparative Example 3) | aqueous | 19.2314 | 26.9658 | 7.7344 | 28.7 |

The composition A1 according to the invention is substantially superior to the conventional composition B1 with respect to the water-repellant effect.

1.1.2. Use-On Leather

For testing the impregnation effect on leather, a leather fiber material was used since this material has surfaces which are more uniform than those of natural leather.

The test liquids (5% strength) are allowed to run over the obliquely positioned test samples (about 45° C.) by means of a pipette until the surface is wet. The samples are then allowed to dry overnight at room temperature. In each case a 0.04 ml water drop is placed on the samples which have been laid out flat and is covered with a piece of glass so that the evaporation of the water drop does not influence the measurement. The time until the drop is completely absorbed is measured. In each case double determinations are carried out.

The penetration time of the drop is stated as the result for the leather which has been rendered water-repellent, cf. tables 4 and 5.

TABLE 4

|  | Untreated | Composition A | Composition B Comparative Example 1 | Composition C Comparative Example 2 |
|---|---|---|---|---|
| Penetration time [min.] | 3 | 45 | 8 | >60 |

The composition A according to the invention is substantially superior to the conventional composition B, and only the benzinic solution (composition C) has a slightly longer water penetration time.

TABLE 5

|  | Untreated | Composition A1 A1 | Composition B1 Comparative Example 3 |
|---|---|---|---|
| Penetration time [min.] | 8 | 45 | 9 |

The composition A1 according to the invention is substantially superior to the conventional composition B1 with respect to the water penetration time.

1.1.3. Use on Cork

The test solutions (5% strength) are allowed to run over the obliquely positioned test samples (about 45° C.) by means of a pipette until the surface is wet. The samples are then allowed to dry overnight at room temperature. The water-repellent effect is determined by measuring the contact angle of a 0.04 ml water drop on the treated surfaces. In each case the mean value of three measurements is determined, cf. table 6.

TABLE 6

|  | Untreated | Composition A | Composition B Comparative Example 1 | Composition C Comparative example 2 |
|---|---|---|---|---|
|  | Contact angle [°] | | | |
| immediately | 75 | 138 | 140 | 133 |
| after 1 min. | 45 | 138 | 102 | 131 |
| after 2 min. | 42 | 138 | 84 | 131 |
| after 3 min. | 40 | 138 | 12 | 129 |
| after 4 min. | 36 | 137 | 72 | 129 |
| after 5 min. | 32 | 136 | 59 | 128 |
| after 6 min. | 30 | 135 | 47 | 127 |
| after 7 min. | 29 | 134 | 40 | 126 |
| after 8 min. | 29 | 133 | 36 | 125 |
| after 9 min. | 29 | 132 | 33 | 124 |
| after 10 min. | 28 | 131 | 30 | 124 |

The composition A according to the invention is superior in the water-repellent effect even to the benzinic formulation C, whereas the emulsifier-containing formulation B has virtually attained the level of the untreated cork after 10 min.

1.2. Testing on Nonporous Surfaces

Determination of the Water Repellency by Means of Contact Angle Measurement:

The contact angle measurements are carried out as follows: a water drop having a volume of 0.01 ml is applied to the surface to be tested from a height of 15 mm, and the contact angle is determined with the aid of a goniometer (type 100-10 from Rame-Hart Inc., New Jersey, USA). The measurement is repeated 4 times, and the mean value of the 5 measurements is calculated. Subsequently, the contact angle measurement on the substrate not treated with the composition according to the invention is defined as the blank value.

By means of a cloth, the compositions A, B and C are applied to a painted metal sheet having a blank value of 66° and rubbed. After allowing to stand for 15 min at room temperature, the contact angle (R1) is measured. Thereafter, tap water having a temperature of about 10° C. is dripped onto the treated substrate 4 times for 15 min from a distance of 20 cm, likewise at room temperature, in each case in an amount of 10 l per 100 cm$^2$ of substrate. In each case after dripping for 15 minutes, the contact angle (R2, R3, R4, R5) is determined again. The result of the contact angle measurement is to be found in tables 7 and 8:

TABLE 7

| Contact angle | Duration of dripping [min] | Composition A | Composition B Comparative Example 1 | Composition C Comparative Example 2 |
|---|---|---|---|---|
|  |  | Contact angle [°] | | |
| R1 | 0 | 89 | 73 | 85 |
| R2 | 15 | 80 | 82 | 82 |
| R3 | 30 | 79 | 78 | 80 |
| R4 | 45 | 75 | 75 | 75 |
| R5 | 60 | 75 | 75 | 75 |

The substantially poorer initial contact angle in the case of the composition B is clearly evident and is caused by the emulsifier contained in the formulation. The composition A according to the invention and the benzinic composition C on the other hand are at the same high level.

TABLE 8

| Contact angle | Duration of dripping [min.] | Composition A1 | Composition B1 Comparative Example 3 |
|---|---|---|---|
| | | Contact angle [°] | |
| R1 | 0 | 77 | 86 |
| R2 | 15 | 81 | 78 |
| R3 | 30 | 82 | 78 |
| R4 | 45 | 82 | 79 |
| R5 | 60 | 82 | 78 |

The composition A1 according to the invention is slightly superior to the emulsifier-containing composition B1 with respect to the contact angle relative to water.

Section B

Examples of the use of the compositions according to the invention in the sizing of paper and in the coating of gypsum plasterboard:

In order to demonstrate the advantage of the claimed, aqueous compositions for the sizing of paper and the imparting of water repellency to gypsum plasterboard, the compositions were tested in comparison with aqueous, emulsifier-containing compositions based in each case on the same active substance, with regard to their effect as sizes and water repellents. Solvent-based compositions were not used for comparison since they are not suitable for use for the abovementioned water-based applications.

Amino-Functional Organopolysiloxanes Used:

Amine Oil 1:

The amine oil 1 has a viscosity of about 1000 mm²/s at 25° C., the functional radicals are —(CH$_2$)$_3$NH(CH$_2$)$_2$NH$_2$ and has an amine number of 0.6 meq/g of organopolysiloxane. In addition, the organopolysiloxane contains about 0.75 mol % of reactive OMe/OH radicals as terminal groups.

Amine Oil 2:

The amine oil 2 has a viscosity of about 1000 mm²/s at 25° C., the functional radicals are —(CH$_2$)$_3$NH(CH$_2$)$_2$NH$_2$ and has an amine number of 0.6 meq/g of organopolysiloxane.

The terminal groups in this case are Me$_3$SiO radicals.

Amine Oil 3:

Amine oil 3 has a viscosity of about 230 mm²/s at 25° C., the functional radicals are —(CH$_2$)$_3$NH(CH$_2$)$_2$NH$_2$, and an amine number of 2.6 meq/g of organopolysiloxane. The terminal groups are likewise Me$_3$SiO radicals in the case of this amine oil.

Amine Oil 4:

Prepared according to example 5 in U.S. 2004/0029981 A1.

The amine oil 4 thus prepared has a viscosity of about 1000 mm²/s at 25° C., the functional radicals —(CH$_2$)$_3$NH(CH$_2$)$_3$NH$_2$, and an amine number of 0.6 meq/g of organopolysiloxane. The terminal groups in this case are Me$_3$SiO radicals.

Preparation of the Various Compositions:

Aqueous Composition A1 According to the Invention:

16 g of amine oil 1 are added to 6 g of water, 6 g of ethylene glycol monobutyl ether and 0.17 g of acetic acid at room temperature while stirring, and the remaining water to a total weight of 100 g is then also incorporated. A milky opaque emulsion is obtained. Depending on the applications, dilution is effected to 4% or 0.2% active substance content with demineralized water.

Aqueous, Emulsifier-Containing Comparative Example B1:

16 g of amine oil 1 are added to 6 g of water, 6 g of organic emulsifier (fatty alcohol ethoxylate having about 6 EO) and 0.17 g of acetic acid at room temperature while stirring, and the remaining water to a total weight of 100 g is then also incorporated. A milky opaque emulsion is obtained. Depending on the application, dilution is effected to 4% or 0.2% active substance content with demineralized water.

Aqueous Composition A2 According to the Invention:

16 g of a mixture of 11.1 g of amine oil 1 and 4.9 g of MQ resin are added to 6 g of water, 6 g of ethylene glycol monobutyl ether and 0.17 g of acetic acid at room temperature while stirring, and the remaining water to a total weight of 100 g is then also incorporated. A milky opaque emulsion is obtained. Depending on the application, dilution is effected to 4% or 0.2% active substance content with demineralized water.

Aqueous, Emulsifier-Containing Comparative Example B2:

16 g of a mixture of 11.1 g of amine oil 1 and 4.9 g of MQ resin are added to 6 g of water, 6 g of organic emulsifier (fatty alcohol ethoxylate having about 6 EO) and 0.17 g of acetic acid at room temperature while stirring, and the remaining water to a total weight of 100 g is then also incorporated. A milky opaque emulsion is obtained. Depending on the application, dilution is effected to 4% or 0.2% active substance content with demineralized water.

Aqueous Composition C1 According to the Invention:

16 g of amine oil 2 are added to 6 g of water and 6 g of ethylene glycol monobutyl ether and 0.17 g of acetic acid at room temperature while stirring, and the remaining water to a total weight of 100 g is then also incorporated. A milky opaque emulsion is obtained. Depending on the applications, dilution is effected to 4% or 0.2% active substance content with demineralized water.

Emulsifier-Containing Aqueous Comparative Example D1:

16 g of amine oil 2 are added to 6 g of water, 6 g of organic emulsifier (fatty alcohol ethoxylate having about 6 EO) and 0.17 g of acetic acid at room temperature while stirring, and the remaining water to a total weight of 100 g is then also incorporated. A milky opaque emulsion is obtained. Depending on the application, dilution is effected to 4% or 0.2% active substance content with demineralized water.

Aqueous Composition C2 According to the Invention:

16 g of a mixture of 11.1 g of amine oil 2 and 4.9 g of MQ resin are added to 6 g of water, 6 g of ethylene glycol monobutyl ether and 0.17 g of acetic acid at room temperature while stirring, and the remaining water to a total weight of 100 g is then also incorporated. A milky opaque emulsion is obtained. Depending on the application, dilution is effected to 4% or 0.2% active substance content with demineralized water.

Emulsifier-Containing, Aqueous Comparative Example D2:

16 g of a mixture of 11.1 g of amine oil 2 and 4.9 g of MQ resin are added to 6 g of water, 6 g of organic emulsifier (fatty alcohol ethoxylate having about 6 EO) and 0.17 g of acetic acid at room temperature while stirring, and the remaining water to a total weight of 100 g is then also incorporated. A milky opaque emulsion is obtained. Depending on the application, dilution is effected to 4% or 0.2% active substance content with demineralized water.

Aqueous Composition E1 According to the Invention:

16 g of amine oil 3 are added to 6 g of water and 0.17 g of acetic acid at room temperature while stirring, and the remaining water to a total weight of 100 g is then also incorporated. A milky opaque emulsion is obtained. Depending on the applications, dilution is effected to 4% or 0.2% active substance content with demineralized water.

Emulsifier-Containing, Aqueous Comparative Example F1:

16 g of amine oil 3 are added to 6 g of water, 6 g of organic emulsifier (fatty alcohol ethoxylate having about 6 EO) and 0.17 g of acetic acid at room temperature while stirring, and the remaining water to a total weight of 100 g is then also incorporated. A milky opaque emulsion is obtained. Depending on the application, dilution is effected to 4% or 0.2% active substance content with demineralized water.

Aqueous Composition E2 According to the Invention:

16 g of a mixture of 11.1 g of amine oil 3 and 4.9 g of MQ resin are added to 6 g of water and 0.17 g of acetic acid at room temperature while stirring, and the remaining water to a total weight of 100 g is then also incorporated. A milky opaque emulsion is obtained. Depending on the application, dilution is effected to 4% or 0.2% active substance content with demineralized water.

Emulsifier-Containing, Aqueous Comparative Example F2:

16 g of a mixture of 11.1 g of amine oil 3 and 4.9 g of MQ resin are added to 6 g of water, 6 g of organic emulsifier (fatty alcohol ethoxylate having about 6 EO) and 0.17 g of acetic acid at room temperature while stirring, and the remaining water to a total weight of 100 g is then also incorporated. A milky opaque emulsion is obtained. Depending on the application, dilution is effected to 4% or 0.2% active substance content with demineralized water.

Aqueous Comparative Example G1:

16 g of amine oil 4 are added to 6 g of water and 6 g of ethylene glycol monobutyl ether and 0.17 g of acetic acid at room temperature while stirring, and the remaining water to a total weight of 100 g is then also incorporated. A milky opaque emulsion is obtained. Depending on the application, dilution is effected to 4% or 0.2% active substance content with demineralized water.

Aqueous Comparative Example G2:

16 g of a mixture of 11.1 g of amine oil 4 and 4.9 g of MQ resin are added to 6 g of water, 6 g of ethylene glycol monobutyl ether and 0.17 g of acetic acid at room temperature while stirring, and the remaining water to a total weight of 100 g is then also incorporated. A milky opaque emulsion is obtained. Depending on the application, dilution is effected to 4% or 0.2% active substance content with demineralized water.

Testing the Sizing Effect on Paper

Treatment of Unsized Paper:

Unsized test papers stored in the laboratory are placed twice, for 5 s each time (front and back 5 s each), on a size liquor diluted to 0.2% active substance content, so that the test paper is completely impregnated with size liquor. The paper impregnated with size liquor is then pushed between two rubber rolls in order to squeeze out excess size solution. Immediately thereafter, the wet squeezed-out paper is reweighed, and the amount of size liquor or active substance applied is calculated from the difference between the masses. Drying is effected for 3 minutes at 150° C. in a circulation drying oven and, for calendering the paper, the paper is ironed using a Rowenta® iron at level 2.5.

Test for Sizing:

After the ironing, the paper is tested for sizing after storage for 2 days at room temperature. For this purpose, pieces measuring 8×8 cm$^2$ are cut out of the sized sheets, folded up at the ends and then placed on an ink solution (highly concentrated green writing ink). The time until 5% of the surface of the test paper is covered with test ink which has struck through is then measured using a stopwatch. The longer the duration, the better the sizing of the paper. For the values in the table below, 0.22% by weight of active substance (amine oil plus any MQ resin), based on paper mass, were applied.

Testing for Water Repellency of Gypsum Plasterboard

Treatment of the Gypsum Plasterboard:

Gypsum plasterboard is coated uniformly by means of a rod applicator with an emulsion diluted to an active substance content of 4%. The amount applied can be controlled by means of the layer thickness of the rod applicator. After coating, the board strip is reweighed, and the amount of treatment emulsion or active substance is determined from the differences between the masses. Drying is then effected for 15 min at 120° C. in a circulation drying oven.

Testing for Water Repellency:

After storage for two days at room temperature, 12×12 cm$^2$ test strips are cut out using a template, and the water absorption according to Cobb (DIN 20535) is determined. The determination of the water absorption according to Cobb is a standard method in the paper industry. Cobb 180 indicates the mass of water in g/m$^2$ of board which the board has absorbed after exposure to water for 180 s. The lower the Cobb value, the better the desired water repellency (reduced water absorption). For the values in the table below, 1 g of active substance/m$^2$ of gypsum plasterboard (active substance=amine oil plus any MQ resin) was always applied; for results, cf. table 9.

TABLE 9

| | A1 | B1 Comparative Example | A2 | B2 Comparative Example | C1 |
|---|---|---|---|---|---|
| Test for sizing (ink flotation time in s) | 25 | 1 | 86 | 3 | 48 |
| Water absorption according to Cobb (Cobb 180 in g/m$^2$) | 50 | 176 | 65 | 98 | 63 |

| | D1 Comparative Example | C2 | D2 Comparative Example | E1 | F1 Comparative Example |
|---|---|---|---|---|---|
| Test for sizing (ink flotation time in s) | 2 | 115 | 5 | 36 | 2 |
| Water absorption according to Cobb (Cobb 180 in g/m$^2$) | 160 | 59 | 89 | 29 | 145 |

| | E2 | F2 Comparative Example | G1 Comparative Example | G2 Comparative Example |
|---|---|---|---|---|
| Test for sizing (ink flotation time in s) | 192 | 11 | 12 | 18 |
| Water absorption according to Cobb (Cobb 180 in g/m$^2$) | 27 | 74 | 140 | 74 |

What is claimed is:

1. A process for treating leather or sizing paper, leather and paper being a substrate, comprising contacting the surface of said substrate with an oil-in-water emulsion, comprising
   (i) 100 parts by weight of a polydimethylsiloxane (P) having aminoalkyl groups and having an amine number of at least 0.1 meq/g of polydimethylsiloxane (P), and comprising units of the formula I $$R^1_a R^2_b SiO_{(4-a-b/2)} \quad (I),$$

in which
   $R^1$ are optionally halogen-substituted alkyl radicals having 1-40 carbon atoms, or are —OR or —OH radicals,
   R are optionally halogen-substituted alkyl radicals having 1-40 carbon atoms,
   $R^2$ are aminoalkyl radicals of the formula II $$-R^3-NR^4R^5 \quad (II),$$

$R^3$ are divalent hydrocarbon radicals having 1-40 carbon atoms,
   $R^4$ are monovalent hydrocarbon radicals having 1-40 carbon atoms or are H,
   $R^5$ is a radical of the formula III $$-(R^6-NR^4)_x R^4 \quad (III),$$

$R^6$ is a divalent radical of the formula IV $$-(CR^4R^4-)_y \quad (IV),$$

x is 0 or a value from 1 to 40,
   y is 1 or 2,
   a is 0, 1, 2 or 3,
   b is 0, 1, 2 or 3 and
   a+b on average is from 1.5 to 2.5, not more than 9 mol % of the radical $R^1$ being OH or OR,
   (ii) at least one MQ silicone resin,
   (iii) at least one protonating agent,
   (iv) water, and
   (v) not more than 5 parts by weight of emulsifier(s),
   and drying the substrate.

2. The process of claim 1, wherein $R^4$ are alkyl radicals having 1 to 6 carbon atoms.

3. The process of claim 1, wherein the radicals $R^2$ are selected from the group consisting of —$(CH_2)N(R^4)_2$, —$(CH_2)_3N(R^4)_2$, —$(CH_2)_3N(R^4)(CH_2)_2N(R^4)_2$, and mixtures thereof.

4. The process of claim 1, further comprising mono- or polyalcohols and ethers thereof, which have a boiling point or boiling range of not more than 260° C. at 0.10 MPa.

5. The process of claim 1, wherein protonating agent(s) are selected from the group consisting of formic acid, acetic acid, sulfuric acid, hydrochloric acid, citric acid, and mixtures thereof.

6. The process of claim 1 containing from 80 mol % to 95 mol % of structural units of the formulae (V) and VI:

$$R^7_3 SiO_{1/2} \quad (V),$$

$$SiO_{4/2} \quad (VI),$$

in which
   $R^7$ are optionally halogen-substituted hydrocarbon radicals having 1-40 carbon atoms or H, —OR or —OH radicals, and the ratio of the units of the general formulae V and VI is from 0.5 to 2.0, and not more than 3% by weight of the radicals $R^7$ are —OR and —OH.

7. The process of claim 1, which contains from 1 to 200 parts by weight of MQ silicone resin based on 100 parts of polydimethylsiloxane (P).

8. The process of claim 1, comprising contact a paper substrate with the aqueous emulsion and drying to form a sized paper.

9. The process of claim 1, wherein treating comprises contacting leather with said aqueous emulsion.

10. The process of claim 1, wherein the protonating agent consists essentially of water soluble acid.

11. The process of claim 1, wherein the protonating agent is a water soluble acid selected from the group consisting of formic acid, acetic acid, sulfuric acid, hydrochloric acid, citric acid, and mixtures thereof.

12. The process of claim 1, wherein no emulsifier is employed.

* * * * *